United States Patent [19]

Meek

[11] 4,213,050
[45] Jul. 15, 1980

[54] SERVO CONTROL FOR X-RAY TOMOGRAPHY

[75] Inventor: Gerrit J. Meek, Eindhoven, Netherlands

[73] Assignee: U.S. Philips Corporation, New York, N.Y.

[21] Appl. No.: 905,224

[22] Filed: May 12, 1978

[30] Foreign Application Priority Data

Jun. 16, 1977 [NL] Netherlands .................. 7706616

[51] Int. Cl.² ........................................... H05G 1/00
[52] U.S. Cl. ................................ 250/445 T; 250/402
[58] Field of Search .................. 250/445 T, 401, 402, 250/522, 523, 490

[56] References Cited

U.S. PATENT DOCUMENTS 3,733,487  5/1973  Louche ........................ 250/445 T

*Primary Examiner*—Craig E. Church
*Attorney, Agent, or Firm*—Thomas A. Briody; Jack Oisher; Jack E. Haken

[57] ABSTRACT

Apparatus for plan-parallel tomography comprises an X-ray tube and detector which are mechanically connected to each other by means of an extendable column consisting of two portions. Linear movement of the X-ray tube is obtained by sliding the two portions during the swiveling of the column. The use of customary servo control arrangements for sliding in or out, however, involves a position error which is approximately proportional to the sliding speed of the column portions. This position error is eliminated by the adding of a correction signals which is proportional to the sliding speed into the servo control signal.

6 Claims, 6 Drawing Figures

SERVO CONTROL FOR X-RAY TOMOGRAPHY

This invention relates to X-ray tomography. More specifically, the invention relates to an examining device, comprising a radiation source, such as $\gamma$ or X-radiation sources, and a radiation detector which are mechanically coupled to each other. The radiation source is connected to one end of a column which can be swiveled by drive means about an axis at the other end of the column, said axis extending perpendicularly to the longitudinal direction of the column and being parallel to and situated at least substantially in a movement plane of the radiation detector. The column comprises two column portions which are movable with respect to each other and whereby the distance between the radiation source and the detector can be adjusted by an electric motor. The electric motor is coupled to a control circuit having a first input which is connected to a position detector wherefrom a feedback signal can be derived. The signal is a measure for the position of the two column portions with respect to each other. A second input of the control circuit is connected to a drive circuit which is coupled to an angle detector wherefrom a detector signal which is dependent of an angle $\alpha$ between the longitudinal direction of the column and a line perpendicular to the movement plane of the radiation detector can be derived. The drive circuit is capable of generating a drive signal for the control circuit which is dependent of the angle $\alpha$.

A device of this kind is known from U.S. Pat. No. 3,733,487. The device described in said Patent comprises a control system for controlling the electric motor connected to the column so that a linear movement is imparted to the X-radiator. The object is to displace the source parallel to the movement plane of the detector. The motor control system described in said Patent produces a linear movement of the X-radiator, however the movement is not parallel to the movement plane of the radiation detector, but rather encloses an angle therewith. As a result, when utilized for tomography procedures, this device produces a tomogram of a layer other than the adjusted and desired layer. The invention eliminates the described drawback.

The invention comprises a drive circuit capable of generating a correction signal which is added to the drive signal and which is proportional to the product of the angle $\alpha$ and the angle derivitive $(d\alpha/dt)$ of the angle $\alpha$. A control circuit thus driven very accurately follows the desired path of the radiation source during the linear movement, so that a tomogram of the desired layer is obtained.

In a preferred embodiment of an examining device in accordance with the invention the drive circuit comprises at least one differentiator circuit for differentiating a drive signal which is dependent on the angle $\alpha$.

In an embodiment of an examining device in accordance with the invention the drive circuit comprises at least one analog-to-digital converter, a memory and a digital-to-analog converter. An input of the analog-to-digital converter is connected to the angle detector and an output of the digital-to-analog converter is connected to the second input of the control circuit; the memory is connected between the output of the analog-to-digital converter and the input of the digital-to-analog converter. The use of digital circuits has been found to be very attractive because arbitrary functions, for example, step functions, can be realized without problems. This is notably important for starting and stopping the motors controlled. Furthermore, offset and drift phenomena are less apparent in digital circuits.

It has been found useful in a tomography device in which a column is connected to a console so as to be rotatable about a swivel axis, to provide the console with drive means for displacing the console together with the column during the swiveling of the column about an axis of rotation which is situated between the radiation source and the radiation detector, the swivel axis coinciding substantially with the movement plane of the radiation detector. The drive means then comprise an electric motor and a control circuit, said control circuit receive a control signal from the drive circuit which comprises a signal which is dependent of the angle $\alpha$, and an associated correction signal which is proportional to $(1+\alpha^2) \cdot d\alpha/dt$.

The invention will be described in detail hereinafter with reference to the accompanying diagrammatic drawing.

FIG. 1 shows an X-ray examining device;

FIG. 2 diagrammatically shows the movements performed by the X-ray examining device;

Figure 1:
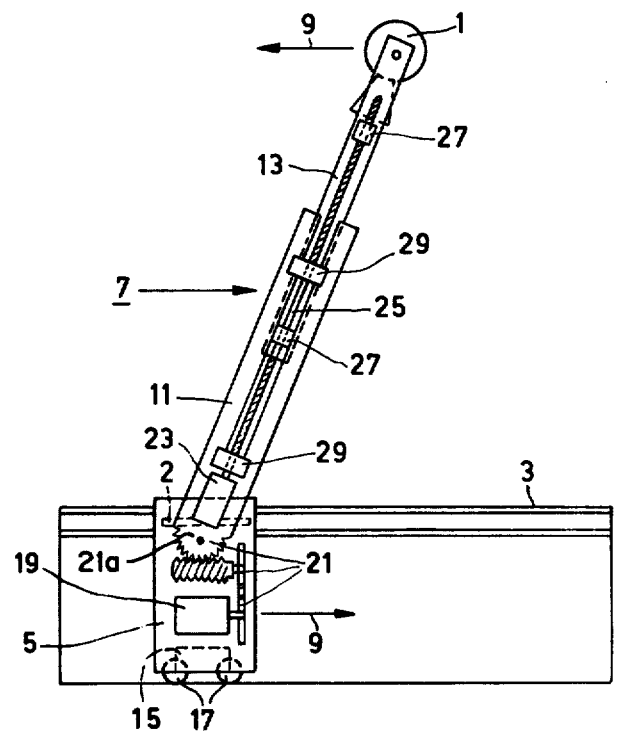

The X-ray examining device shown in FIG. 1 comprises an X-ray tube 1 and an X-ray detector 2, for example, a film cassette. The X-ray tube 1 is supported by a column 7 which is connected to a console 5. The console 5 also supports the detector 2. The X-ray tube 1 and the detector 2 move in opposite directions, preferably parallel to each other, as indicated arrows 9 to produce a tomograph of an object arranged on a table 3. To this end, the console 5 is displaced, for example, to the right and the column 7 is swiveled to the left about axis 21a. In order to enable displacement of the X-ray tube 1 parallel to the detector 2, the column 7 is composed of two column portions 11 and 13 which slide into the other during the swiveling motion of the column 7. The drive means for the displacement of the console 5, the swiveling of the column 7, and the sliding in and out of the column portions 11 and 13 must be accurately coordinated with each other other in order to obtain an accurate tomogram.

The console 5 is displaced by means of an electric motor 15 which drives wheels 17. The column 7 is swiveled by means of an electric motor 19 which is coupled to the column portion 11 by worm-wheel gearing 21.

A third electric motor 23 being connected to the column portion 11, drives a spindle 25 which in conjunction with guide nuts 27 on the column portion 13, is capable of displacing the column portions 11 and 13 relative to each other. The spindle 25 is furthermore journalled in sleeves 29 in order to prevent undesirable bending or swinging of the spindle 25. The detector 2 can be coupled to the X-radiator 1 in known manner by means of a coupling rod, for example, as described in U.S. Pat. No. 3,733,487. The drive 15, 17 of the console 5 will then be superfluous.

Figure 2:
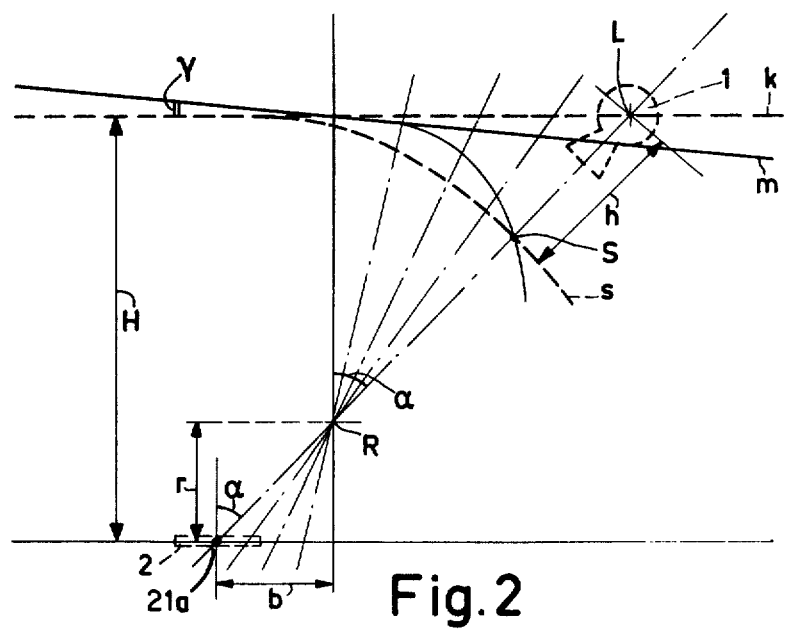

FIG. 2 in principle shows the movement pattern of the tomography device shown in FIG. 1. The detector 2 of FIG. 1 is displaced along the flat table 3 by means of the mobile console 5. The column 7 connected to the console 5 performs a swiveling movement about axis 21a, with the result that the X-ray tube 1 connected to the opposite end of column 7 performs a movement which opposes that of the moving detector 2. The degree of displacement of the console with respect to that of the radiator determines the position of the focus plane of the tomogram. If the console displacement b is related to the column swivel angle α by the equation b=r tan α the column center line will effectively rotate about a point R and the focus plane will be spaced a distance r from axis 21a.

In order to obtain a parallel movement along a path the X-ray tube 1 and the detector 2, such as required for tomography, the column portion 13 must slide in or out, so that the center of the X-ray tube 1 can follow the line k. If there is no sliding, the X-ray tube 1 would follow the line a and arrive in the point S instead of the desired point L on the line k. Therefore, the column portion 13 should be slid out over a distance h=H (1−cos α) cos$^{-1}$ α. The length of the column 7 equals h when the column 7 is perpendicular to the table 3, and α is the complement of the angle between the column 7 and the table 3. The speed v at which the column portion 13 is slid is v=dh/dt=π(H sin α·cos$^{-2}$ α·d α/dt)/180. Therefore, at the instant at which the column 7 is perpendicular to the table 3, α equals zero and so does the speed v.

U.S. Pat. No. 3,733,487 proposes a servo control arrangement for sliding out the upper column portion in a manner adapted to the angle α. The servo control arrangement has the known transmission function H (s)=K[(s+ω$_1$)s]$^{-1}$, in which K and ω$_1$ are constants and s represents the complex frequency. It has been found that, when use is made of such a control arrangement, a deviation still occurs between the ideal path k and the path actually followed by the X-ray tube 1. It has been found that the positioning error e$_1$(t) can be rather accurately described (for α<25°) by the formula:

$$e_1(t) = \omega_1 \cdot K^{-1} dh/dt = \omega_1 v \cdot k^{-1}$$

The positioning error e$_1$(t), therefore, is proportional to the speed v (determined by α and dα/dt) at which the column portion 13 is slid out. If the angle variation d α/dt is constant, the error is $$e_1(t) = \omega_1 \pi H(\sin \alpha)/(K_1 180)$$

For a sufficiently small α:

$$e_1(t) = \omega_1 \pi H \alpha(t)/(K_1 180).$$

The path m followed by the X-ray tube 1, therefore, encloses an angle α with the ideal path k.

The instantaneous speed v$_c$ of the console as a function of the swivel angle equals $$v_c = db/dt = (\pi r(1 + \tan^2 \alpha) d\alpha/dt)/180$$

If a servo control arrangement is used to coordinate the console displacement and column swiveling motions the console will be subject to a position error e$_2$(t) which is determined by the formula:

$$e_2(t) = (\omega_2 \pi r(1 + \tan^2 \alpha) d\alpha/dt)/180 K_2)$$

Tomograms are preferably made in as short period of time as possible in order to avoid blurring due to movements of the patient. Rapid variation of the angle α is thus desired for given exposures. However the associated high d α/dt results in a tomogram of an undesired plane due to the position errors of the X-ray tube and the console 5 which are caused by the inadequate following of the control signals by the servo control arrangement.

Figure 3:
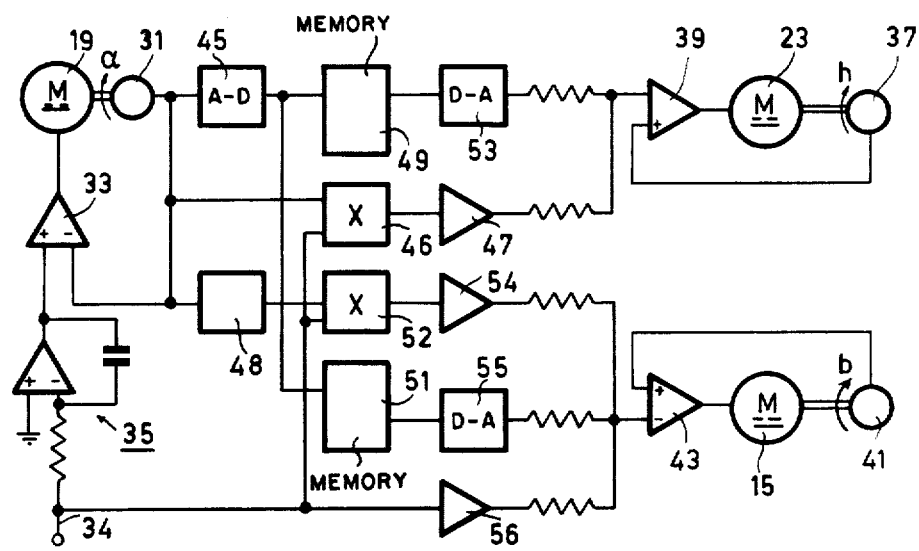
FIG. 3 shows a block diagram of an electronic control of an examining device.

FIG. 3 shows a block diagram of a circuit for controlling an examining device whereby the described position errors are substantially eliminated. The circuit comprises three known servo control arrangements: a first arrangement for the swiveling of the column 7, a second arrangement for sliding out the column portion 13, and a third arrangement for displacing the console 5.

The latter two servo control arrangements are tuned to the first arrangement. The first servo control arrangement comprises the electric motor 19, an angle detector 31 which is mechanically coupled thereto and which generates a signal which is proportional to the angle α, and a differential amplifier 33. The differential amplifier 33 is controlled via an integrator circuit 35, an input 34 of which receives a signal d α/dt which measures the angular velocity at which the column 7 is swiveled. The signal d α/dt may be, for example, a squarewave signal, the angle α completed then increasing or decreasing linearly as a function of the time. The angle detector 31 may be, for example, a linear potentiometer and supply a voltage which is directly proportional to the angle α.

The servo control arrangement for sliding the column portion 13 comprises an electric motor 23, a position detector 37 which is coupled to the electric motor 23, and a differential amplifier 39 having an input which is connected to the position detector 37. The servo control arrangement for the displacement of the console 5 is similarly constructed and comprises an electric motor 15, a position detector 41, and a differential amplifier 43. The movements of the column 7, the column portion 13 and the console 5 are tuned to each other as follows. The detector 31 signal, proportional to the angle α, is digitised by an analog-to-digital converter 45. To this end, the input of the analog-to-digital converter 45 is connected directly to the angle detector 31. The output of the converter 45 is connected to the inputs of the memories 49 and 51. The digital output signal of the converter 45 forms an address at which a digital number is stored in the memory 49. The number corresponds to the digitised control signal (i.e. subdivided into discrete steps) for realizing the sliding out h=H(1−cos α)/cos α associated with instantaneous value of the angle α. The number selected from the memory 49 is applied, via a digital-to-analog converter 53, in analog form to the input of the differential amplifier 39. The capacity of the memory 49 is directly proportional to the number of discrete steps in which the angle α to be covered is sub-divided.

The memory 51 stores the numbers by means of which the servo control arrangement (15, 41, 43) of the console 5 is controlled via the digital-to-analog converter 55. The digitised signals, proportional to the angle α, again form an address at which the digital number corresponding to the control signal is stored in the memory 51. The number is proportional to the control signal for realizing the displacement (b=r tan α) of the console 5. In order to eliminate the position error of the X-ray tube 1 (FIG. 1)

$$e_1(t)=(\pi\omega_1 \sin\alpha d\alpha/dt)/(180K_1 \cos^2\alpha)$$

use is made of an analog multiplier 46 and an amplifier 47. The input 34 is connected to a first input of the multiplier 46, and the angle detector 31 is connected to a second input thereof. The output signal of the multiplier 46 is proportional to $\alpha \, d\alpha/dt$ and, after amplification by the amplifier 47, it constitutes an approximation of the position error $e_1(t)$ which is sufficient for compensating this error. To this end, the output signal of the amplifier 47 on the input of the amplifier 39 is added to the output signal of the digital-to-analog converter 53.

The position error of the console 5 (FIG. 1) $e_2(t)=(\pi\omega_2 r(1+\tan^2\alpha)d\alpha/dt)/(K_2 180)$ is eliminated in the same manner. Two inputs of an analog multiplier 48 are connected to the angle detector 31. The output signal of the multiplier 48 is multiplied by a signal proportional to $d\alpha/dt$ in an analog multiplier 52. After suitable amplification by an inverting amplifier 54, the product proportional to $\alpha^2 d\alpha/dt$ on the input of the amplifier 43 is added to the signal originating from the digital-to-analog converter 55. Furthermore, on the same input a signal proportional to $d\alpha/dt$ is added, said signal being applied to the input of the amplifier 43 via amplifier 56. The position error $e_2(t)$ has thus been compensated for by a suitable approximation which is proportional to $(1+\alpha^2)d\alpha/dt$.

The capacity of the memories 49 and 51 (read only memories or programmed read only memories) is determined by the number of discrete steps in which the angle $\alpha$ is sub-divided and by the accuracy of the digital numbers, representing the control signal, stored at each address. Obviously, as the discreteness is more refined, the servo control will be more accurate.

Figure 4:
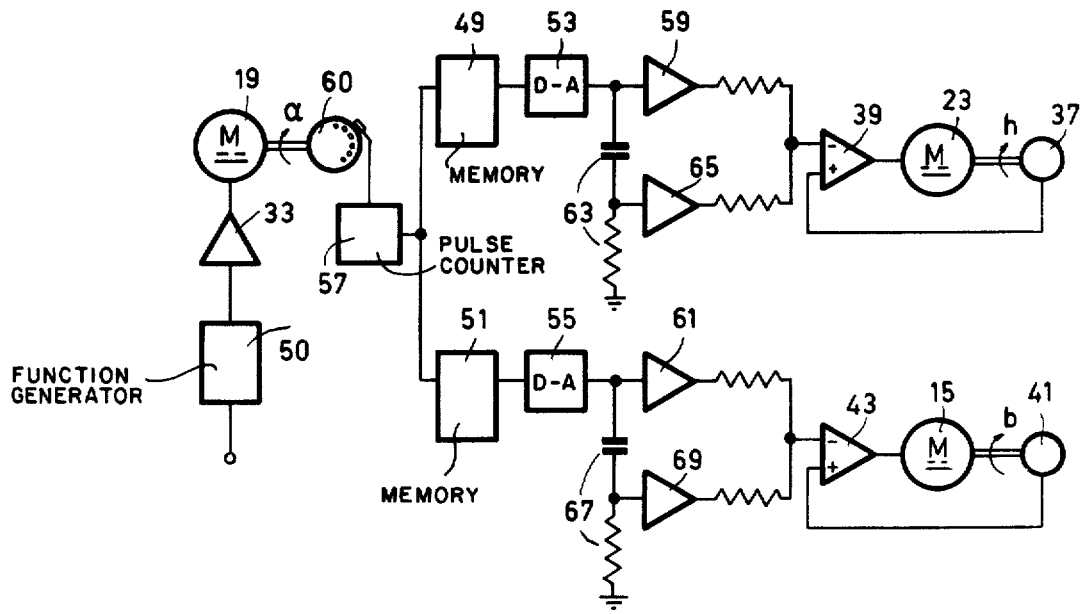
FIG. 4 shows a block diagram of a preferred embodiment of a control arrangement for an examining device.

FIG. 4 shows an embodiment of a circuit arrangement which does not require analog multipliers. The circuit comprises two servo control arrangements (23, 37 and 39) for sliding out the column portion 13 and (15, 41 and 43) for displacing the console 5. The swiveling of the column 7 is achieved by an open loop control system which comprises a function generator 50, an amplifier 33 and an electric motor 19. The function generator 50 produces smooth starting and stopping of the motor 19 during the swiveling of the column 7 and will be described hereinafter. A pulse generator 60 is coupled to the electric motor 19, said generator supplying a number of pulses proportional to the angle $\alpha$. The pulses are converted, by way of a digital pulse counter 57, into a digital word which represents an address of the memories 49 and 51. The memories 49 and 51 contain, respectively, the numerical value $(1-\cos\alpha)/\cos\alpha$ for the sliding out of the column portion 13, and the numerical value $(\tan\alpha)$ for displacement of the console 5. The memories 49 and 51 are actuated in parallel by the address formed by the pulse counter 57, so that the values $(1-\cos\alpha)/\cos\alpha$ and $(\tan\alpha)$, stored in the memory sections are applied, via the digital-to-analog converters 53 and 55, respectively, and via amplifiers 59 and 61, respectively, to the servo control arrangements (23, 37, 39) and (15, 41, 43). The amplifier 59 has an adapted gain, like the amplifier 61. In order to eliminate the position error $e_1(t)$ of the X-ray tube 1, the output signal of the digital-to-analog converter 53 is applied, via a differentiating R-C network 63 and an amplifier 65, to the servo control arrangement (23, 37, 39). Because the position error $e_1(t)$ is proportional to the speed of sliding out of the column portion 13, the correction signal can be obtained in the described simple manner. An identical differentiating R-C network 67 and an amplifier 69 having an adapted gain are used for the elimination of the position error $e_2(t)$ of the console 5.

The digital-to-analog converters 53 and 55, the memories 49 and 51 and the digital pulse counter 57 may obviously be replaced by analog multipliers, adders and the like as described in said United States Patent Specification. The advantage thereof consists in that the angle $\alpha$ need no longer be sub-divided into discrete steps, so that no quantizing errors occur. A known drawback of this analog substitution consists in the errors caused by the offset and drift voltages whose effect is greater in analog circuits than in digital circuits.

Figure 5:
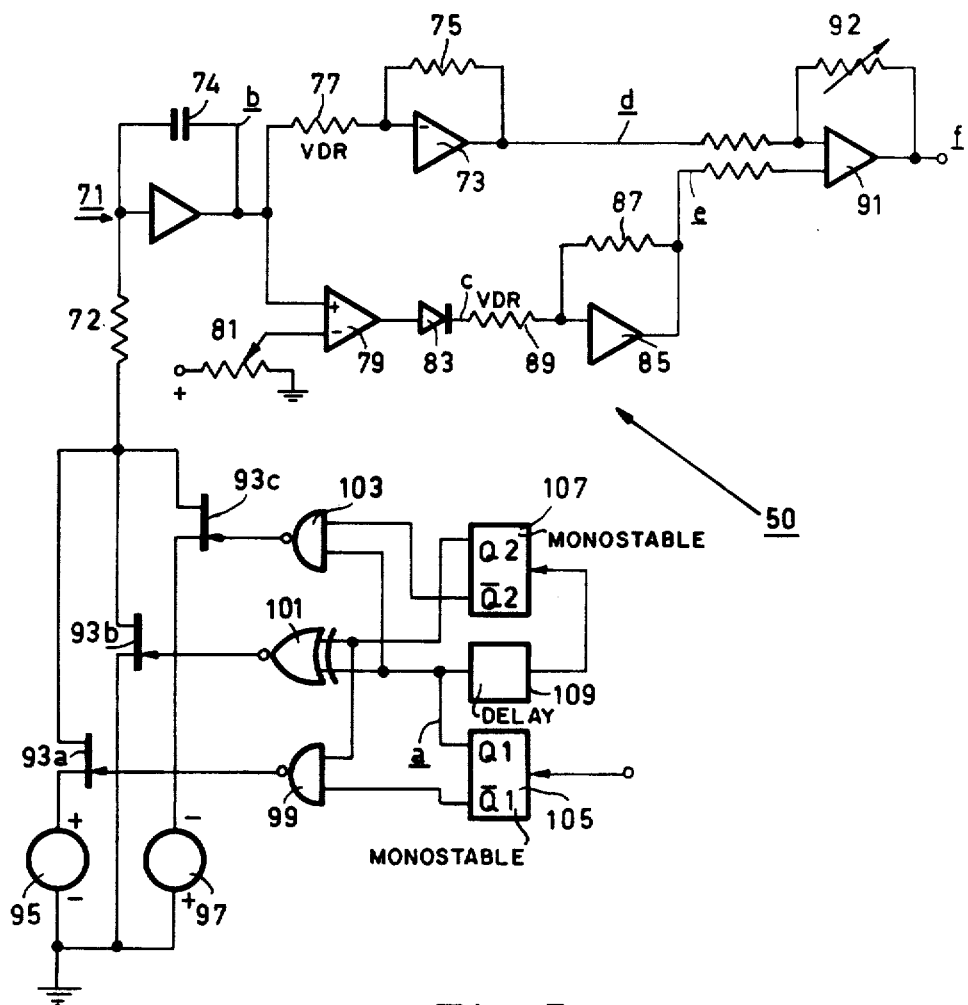
FIG. 5 shows a function generator for the control arrangement shown in FIG. 4.
Figure 6:
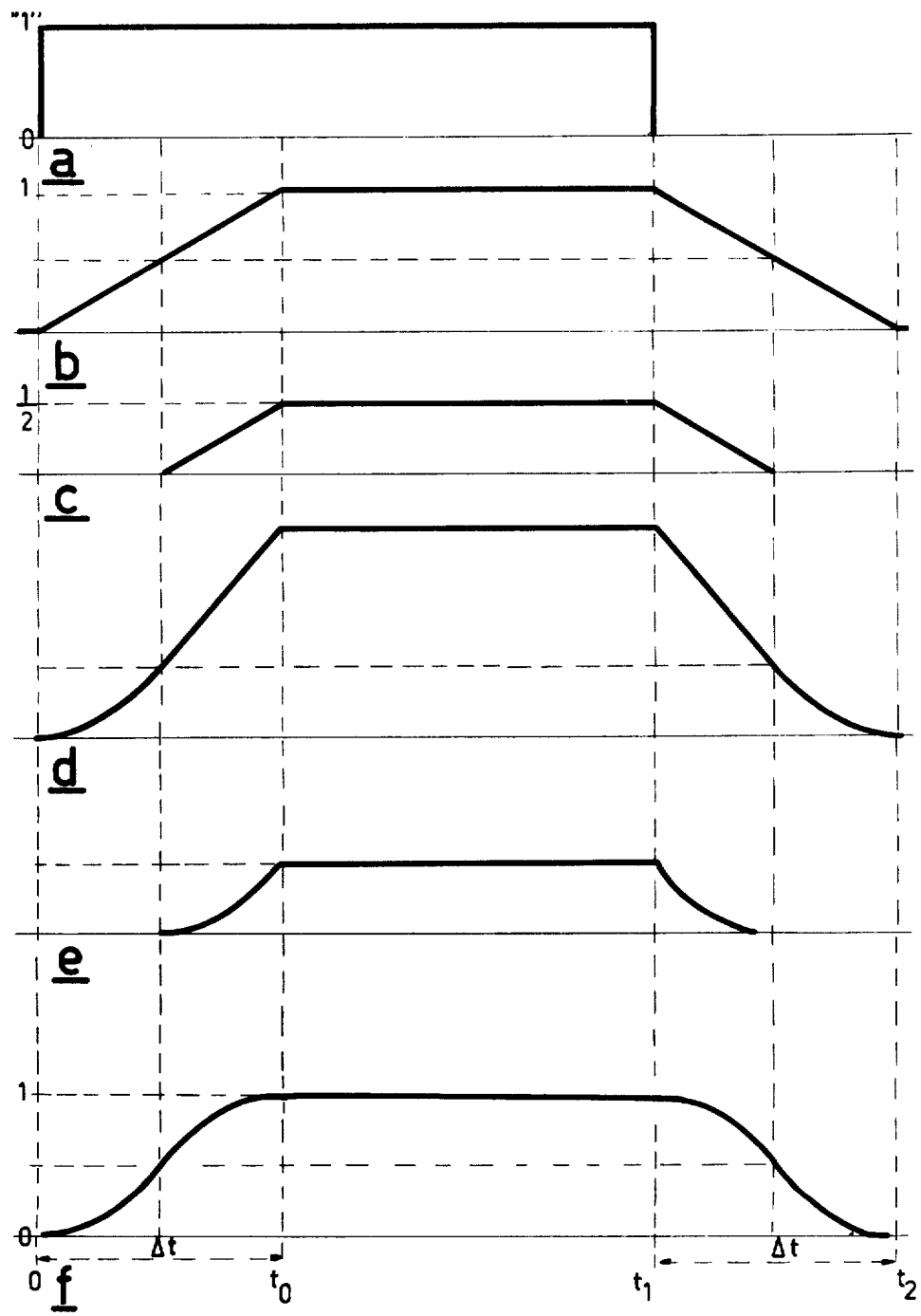
FIG. 6 shows time diagrams of the voltages occurring at different points in the generator of FIG. 5.

The function generator 50 shown in FIG. 5 serves to smooth the starting and stopping of the swiveling of the column 7 by means of electric motor 19 (FIGS. 3 and 4). The function generator 50 comprises an integrator 71 for generating a trapezoidal voltage b (FIG. 6) in a manner to be described. The trapezoidal voltage b is amplified in a first network, to form the waveform d (FIG. 6) shown in FIG. 6 by a non-linear amplifier. The non-linear amplifier comprises an amplifying element 73, a resistor 75 and a voltage-dependent resistor 77. In a second network, a constant voltage, adjustable by means of a potentiometer 81, is subtracted from the waveform b in a differential amplifier 79. A diode 83 blocks any negative voltage occurring on the output of the differential amplifier 79. The positive voltage c (FIG. 6) occurring behind the diode is amplified via a non-linear amplifier which comprises an ampliying element 85, a resistor 87 and a voltage-dependent resistor 89. The voltage e (FIG. 6) thus obtained is subtracted from the voltage d in a differential amplifier 91. The differential signal f thus produced, whose amplitude is adjustable by means of the potentiometer 92, comprises a smooth starting and stopping part between the minimum (0) and the maximum (1) constant value and is used for controlling the amplifier 33 to ensure smooth driving by the electric motor 19 without abrupt movements.

The trapezoidal voltage b is generated as follows. A starting pulse is applied to a monostable multivibrator 105. The outputs of the multivibrator 105, $Q_1$ and $\overline{Q}_1$, carry the values "1" and "0", respectively, (a in FIG. 6) during the period from $t=0$ until $t=t_1$. The signal a starts a second, delayed-action monostable multivibrator 109 which, after a period of time $\Delta t$ (at the instant $t_o$), starts a third monostable multivibrator 107. The outputs $Q_2$ and $\overline{Q}_2$ of the multivibrator 107 thus have the value "1" and "0", respectively, from $t=t_o$ untill $t=t_2$. The outputs $Q_1$, $\overline{Q}_1$, $Q_2$ and $\overline{Q}_2$ are connected to inputs of inverting OR-gates 99, 103 and an EXCLUSIVE-OR gate 101, whose outputs actuate the semiconductor switches 93a, 93b or 93c. An input resistor 72 of the integrator 71 is connected via the switches 93a, 93b or 93c, to either a positive source 95, to a negative source 97, or to ground. This is effected in sequence so that the integrator 71 is connected to the positive source 95 from $t=0$ until $t=t_o$, to ground between $t=t_o$ and $t=t_1$, and to the negative source 97 between $t=t_1$ until $t=t_2$. Prior to $t=0$ and after $t=t_2$, the integrator 71 is also connected to "zero" via the semiconductor switch 93b.

What is claimed is:

1. In an examining device comprising:
a source of penetrating radiation; a radiation detector which is movable in a plane; a column having a first end coupled to the source and a second end coupled to the detector, the column comprising two column portions which are movable with respect to each other along the longitudinal direction of the column; movement means which function to move the column portions with respect to each other; swiveling means which function to swivel the column about an axis which extends perpendicular to the longitudinal direction of the column, parallel to and substantially in the movement plane of the raidation detector; a position detector which produces a feedback signal which is a measure of the position of the two column portions with respect to each other; drive circuit means which function to produce an angle signal which is a function of the angle $\alpha$ between the longitudinal direction of the column and a line perpendicular to the movement plane of the detector; and a control circuit having an output connected to operate the movement means, a first input connected to receive the feedback signal and a second input connected to receive the angle signal; the improvement wherein:

the drive circuit means further function to generate a correction signal which is substantially proportional to the product of the angle $\alpha$ multiplied by the rate of change of the angle $\alpha$, d $\alpha$/dt, and to supply the sum of the angle signal and the correction signal to the control circuit.

2. An examining device as claimed in claim 1, wherein the drive circuit means comprise at least one differentiator circuit connected to differentiate the angle signal.

3. An examining device as claimed in claim 2 or 1, wherein the drive circuit means comprise at least one analog multiplier, a first input of which is connected to receive a signal proportional to the angle $\alpha$ and a second input of which is connected to receive a signal which is proportional to d $\alpha$/dt.

4. An examining device as claimed in claim 2 or 1 wherein the drive circuit means comprise at least one digital counter, a read-only memory connected to the output of said counter, and a digital-to-analog converter which is connected to the output of the read-only memory.

5. An examining device as claimed in claim 1 or 2 wherein the drive circuit means comprise a series connection of an analog-to-digital converter, a read-only memory (ROM) and a digital-to-analog converter.

6. An examining device as claimed in claim 1 further comprising a console connected to the column and drive means which function to displace the console as the column swivels to produce a rotation of the column center line about a point situated between the source and the detector, the drive means being connected to receive a control signal from the drive circuit means, which signal is determined by the angle $\alpha$ and a second correction signal which is proportional to $(1+\alpha^2)$ d $\alpha$/dt.

* * * * *